United States Patent
Moussy et al.

(10) Patent No.: US 8,153,792 B2
(45) Date of Patent: Apr. 10, 2012

(54) PROCESS FOR THE SYNTHESIS OF 2-AMINOTHIAZOLE COMPOUNDS AS KINASE INHIBITORS

(75) Inventors: Alain Moussy, Paris (FR); Philippe Reginault, Fontaine-les-Dijon (FR); François Bellamy, Saulon Larue (FR); Anne Lermet, Villeurbanne (FR)

(73) Assignee: AB Science, Paris (FR)

( * ) Notice: Subject to any disclaimer, the term of this patent is extended or adjusted under 35 U.S.C. 154(b) by 93 days.

(21) Appl. No.: 12/526,827

(22) PCT Filed: Feb. 13, 2008

(86) PCT No.: PCT/EP2008/051704
§ 371 (c)(1),
(2), (4) Date: Aug. 12, 2009

(87) PCT Pub. No.: WO2008/098949
PCT Pub. Date: Aug. 21, 2008

(65) Prior Publication Data
US 2010/0121063 A1    May 13, 2010

Related U.S. Application Data

(60) Provisional application No. 60/889,587, filed on Feb. 13, 2007.

(51) Int. Cl.
C07D 417/04 (2006.01)
C07D 277/28 (2006.01)
C07D 401/14 (2006.01)

(52) U.S. Cl. .................. 544/364; 546/270.4; 548/190; 548/198

(58) Field of Classification Search .................. None
See application file for complete search history.

(56) References Cited

U.S. PATENT DOCUMENTS

| 3,299,087 A | 1/1967 | Spivack et al. | |
|---|---|---|---|
| 2005/0239852 A1* | 10/2005 | Ciufolini et al. | 514/370 |
| 2007/0003252 A1* | 1/2007 | Kuo et al. | 386/96 |

FOREIGN PATENT DOCUMENTS

| AU | 2004309248 | | 7/2005 |
|---|---|---|---|
| WO | WO 03/002105 | A2 | 1/2003 |
| WO | WO 03/002106 | A2 | 1/2003 |
| WO | WO 03/002107 | A2 | 1/2003 |
| WO | WO 03/002108 | A2 | 1/2003 |
| WO | WO 03/002109 | A2 | 1/2003 |
| WO | WO 03/002114 | A2 | 1/2003 |
| WO | WO 03/003004 | A2 | 1/2003 |
| WO | WO 03/003006 | A2 | 1/2003 |
| WO | WO 03/004006 | A2 | 1/2003 |
| WO | WO 03/004007 | A2 | 1/2003 |
| WO | WO 03/035049 | A2 | 5/2003 |
| WO | WO 03/035050 | A2 | 5/2003 |
| WO | WO 03/039550 | A1 | 5/2003 |
| WO | WO 03/072090 | A2 | 9/2003 |
| WO | WO 03/072106 | A2 | 9/2003 |
| WO | WO 2004/014903 | A1 | 2/2004 |
| WO | WO 2004/076693 | A1 | 9/2004 |
| WO | WO 2005/046323 | A2 | 5/2005 |

OTHER PUBLICATIONS

Vippagunta et al. Advanced Drug Delivery Reviews 48 (2001), pp. 3-26.*
Broudy, V. "Blood: Stem Cell Factor and Hematopoiesis", The Journal of the American Society of Hematology, vol. 90, No. 4, Aug. 15, 1997, pp. 1345-1364.
Crank, G. et al. "Formation of Thioamide Derivative from Reactions of Isothiocyanates with Oxazol-2-amines", Aust. J. Chem., vol. 38, 1985, pp. 447-458.
Beghini, A. "Blood: C-kit mutations in core binding factor leukemias", The American Journal of the American Society of Hematology, vo. 95, No. 2, Jan. 15, 2000, pp. 726-728.
Longley, J. et al. "Somatic c-Kit activating mutation in urticaria pigmentosa and aggressive mastocytosis: establishment of clonality in a human mast cell neoplasm", Nature Genetics, vol. 12, Mar. 1996, pp. 312-314. Longley, J. et al. "Classes of c-KIT activating mutations: proposed mechanisms of action and implications for disease classification and therapy", Leukemia Research, vol. 25, 2001, pp. 571-576.
Kim, K. et al. "Inhibition of vascular endothelial growth factor-induced angiogenesis suppresses tumor growth in vitro", Nature, vol. 362, Apr. 29, 1993, pp. 841-844.
Maziere, M. et al. "Derives fluoroaryles de quelques heterocycles", A La Societe Chimique, pp. 1000-1003.
Singh, S. et al. "Studies in Hantzsch thiazole systhesis: Part 2—Reactions of thiocarboxamides with α-haloketones", Indian Journal of Chemistry, vol. 29B, Jun. 1990, pp. 533-538.

(Continued)

*Primary Examiner* — Kamal Saeed
*Assistant Examiner* — Nyeemah A Grazier
(74) *Attorney, Agent, or Firm* — Hamre, Schumann, Mueller & Larson P.C.

(57) ABSTRACT

The present invention relates to an industrial process of preparing pharmaceutical compounds having the formula (1) which are useful as certain tyrosine kinase inhibitors and more particularly as c-kit and bcr-abl inhibitors. The groups R1 and R2, identical or different, represent each a hydrogen, halogen atom, an alkyl, an alkoxy, a trifluoromethyl, an amino, an alkylamino, a dialkylamino, a solubilising group; m is 0-5 and n is 0-4; the group R3 represents an aryl or an heteroaryl group as described in claims herein.

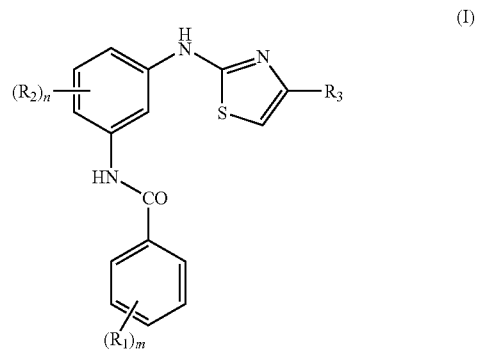

22 Claims, 2 Drawing Sheets

OTHER PUBLICATIONS

Rajappa, S. et al. "Selective Functionalization in a 2-Nitro-*p*-phenylenediamine: Part II—Synthesis of Derivatives of 5-(2-Thiazolylamino)-benzimidazole 2-Carbamates", Indian Journal of Chemistry, vol. 19B, Jul. 1980, pp. 536-538.

Funnell, R. et al. "A Study of Three Reactions leading to Isomeric 2-(*N,N*-Disubstituted Amino)thiazol-5-yl Keytones", J. Chem. Soc., 1987, pp. 2311-2315.

Caira, M. "Crystal Polymorphism—Theoretical Principles and Practical Implications", Topics in Current Chemistry, vol. 198, 1998, pp. 164-208.

Taurins et al. "Synthesis of Pyridyl- and Quinolyl-Substituted 2-Aminothiazoles (1)". Department of Chemistry, McGill University, (Oct. 1970), vol. 7, pp. 1137-1141.

* cited by examiner

PROCESS FOR THE SYNTHESIS OF 2-AMINOTHIAZOLE COMPOUNDS AS KINASE INHIBITORS

The present invention relates to an industrial process of synthesizing of pharmaceutical compounds having the formula 1:

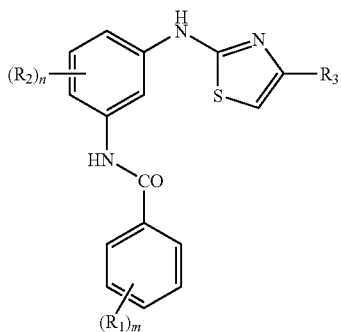

(I)

which are useful as certain tyrosine kinase inhibitors and more particularly as c-kit and bcr-abl inhibitors. The groups R1 and R2, identical or different, represent each a hydrogen, halogen atom, an alkyl, an alkoxy, a trifluoromethyl, an amino, an alkylamino, a dialkylamino, a solubilising group; m is 0-5 and n is 0-4; the group R3 represents an aryl or an heteroaryl group as described in claims herein.

BACKGROUND OF THE INVENTION

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation.

As of today, there are about 58 known receptor tyrosine kinases. Included are the well-known VEGF receptors (Kim et al., Nature 362, pp. 841-844, 1993), PDGF receptors, c-kit, Flt-3 and the FLK family. These receptors can transmit signals to other tyrosine kinases including Src, Raf, Frk, Btk, Csk, Abl, Fes/Fps, Fak, Jak, Ack, etc.

Among tyrosine kinase receptors, c-kit is of special interest. Indeed, c-kit is a key receptor activating mast cells, which have proved to be directly or indirectly implicated in numerous pathologies for which the Applicant filed WO 03/004007, WO 03/004006, WO 03/003006, WO 03/003004, WO 03/002114, WO 03/002109, WO 03/002108, WO 03/002107, WO 03/002106, WO 03/002105, WO 03/039550, WO 03/035050, WO 03/035049, WO 03/0720090, WO 03/072106, WO 04/076693 and WO 2005/016323.

We found that mast cells present in tissues of patients are implicated in or contribute to the genesis of diseases such as autoimmune diseases (rheumatoid arthritis, inflammatory bowel diseases (IBD)) allergic diseases, bone loss, cancers such as solid tumors, leukaemia and GIST, tumor angiogenesis, inflammatory diseases, interstitial cystitis, mastocytosis, graft-versus-host diseases, infection diseases, metabolic disorders, fibrosis, diabetes and CNS diseases. In these diseases, it has been shown that mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-α, GM-CSF, MIP-1a, MIP-1b, MIP-2 and IFN-γ).

The c-kit receptor can also be constitutively activated by mutations leading to abnormal cell proliferation and development of diseases such as mastocytosis (D816V mutation) and various cancers such as GIST (c-kitΔ27, a juxtamembrane deletion).

Furthermore, 60% to 70% of patients presenting with AML have blasts which express c-kit, the receptor for stem cell factor (SCF) (Broudy, 1997). SCF promotes growth of hematopoietic progenitors, and act as a survival factor for AML blasts. In some cases (1 to 2%) of AML, a mutation in a conserved residue of the kinase domain (Kit816) resulting in constitutive activation of c-kit has been described (Beghini et al., 2000; Longley et al., 2001). This gain of function mutation (Asp to Val/Tyr substitution) has been identified in mast cell leukemic cell lines and in samples derived from patients with mastocytosis (Longley et al., 1996).

In addition, we have studied about 300 patients afflicted with systemic mastocytosis and we have shown that the Kit816 mutation is expressed in about 60% of cases. In this regard, we filed WO 04/076693 which relates to tailored treatment of the different forms of mastocytosis depending on the presence or absence of the Kit816 mutation.

Thus, we recently have proposed to target c-kit to deplete the mast cells responsible for these disorders. We discovered in this regard, new potent and selective c-kit inhibitors which are 2-(3-aminoaryl)amino-4-aryl-thiazoles described in our PCT application WO 2004/014903.

The synthesis of substituted 2-aminothiazole is known from literature. In the following publications the general synthesis of these compounds are usually obtained using a two-stage scheme, including bromination of the initial ketones (A) (G. Crank and R. Kahn, Austr. J. Chem, 38(3), 447-458 (1985)) followed by cyclocondensation of the intermediate α-bromoketones (C) with thiourea (B) by refluxing in ethanol or methanol (M. Maziere et al, Bull. Soc. Chim. France, 1000-1003 (1963); J. D. Spivack U.S. Pat. No. 3,299,087).

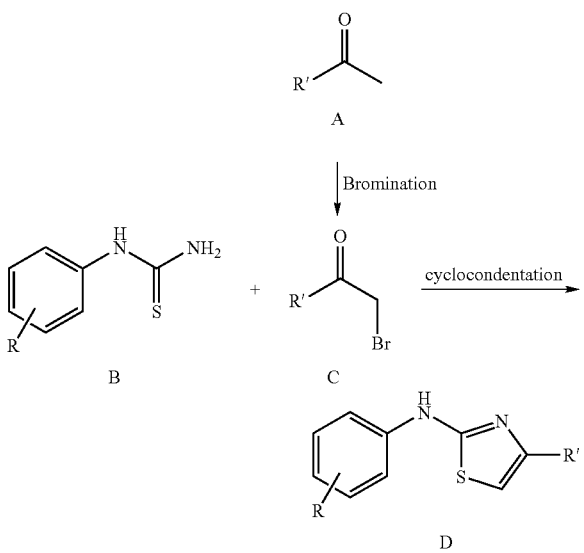

Scheme I

However, when R is an electron withdrawing groups like nitro functionality, the yield of cycloaddition do not exceed 65% (S. P. Singh et al, Indian j. Chem. Sect. B, 29 (6), 533-538, (1990)). This disadvantage is probably due to the instability of the nitroarylthiourea, which leads to the formation of both impurity and highly reactive by-product, when reacting in the presence of a base.

It is apparent from the above, that this methodology applied to nitroarylthiourea has synthetic disadvantages concerning one or more of these characteristics: yield, scalability to multi-gram synthesis and purifications.

SUMMARY

Our aim was to elaborate an industrial applicable process, in which good yields are obtained involving simple industrial operations.

We found that reacting acetylated nitroarylthiourea with α-bromoketoaryl at room temperature, in methanol and in the presence of base such as potassium carbonate give the desired thiazole after 3-6 h in excellent yield (90-97%).

In addition, pure thiazoles were obtained by simple filtration after addition of water to the reaction mixture.

Therefore, the present invention provides a new and industrial process for the synthesis of 2-amino(nitroaryl) thiazole in good yield by reacting a stable acetylated nitroarylthiourea with α-bromoketoaryl in mild conditions.

DETAILED DESCRIPTION

Figure 1:
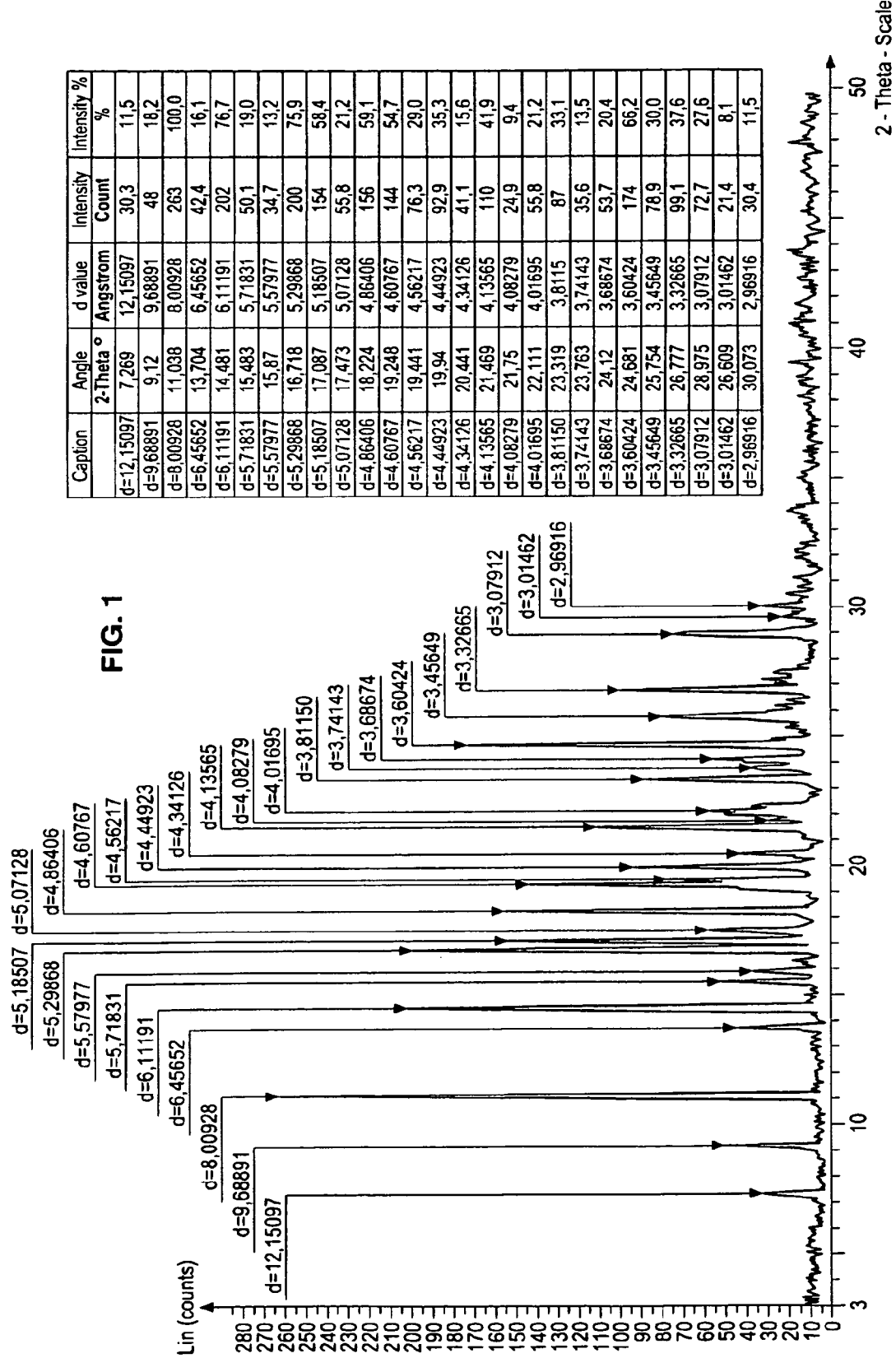
FIG. 1 shows an X-ray diffraction pattern of a polymorph of the methanesulfonic acid salt of N-[4-Methyl-3-(4-pyridin-3-yl-thiazol-2-ylamino)-phenyl]-benzamide of formula (IX).

The invention is aimed at a process for manufacturing a compound of formula (I):

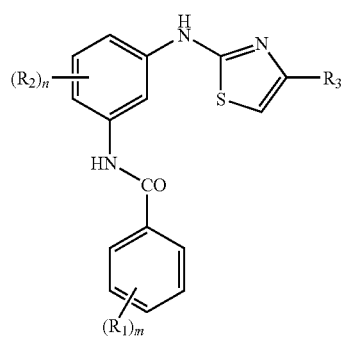

Or a salt, or a solvate thereof, wherein

R1 and R2 are selected independently from hydrogen, halogen, a linear or branched alkyl, cycloalkyl group containing from 1 to 10 carbon atoms, trifluoromethyl, alkoxy, cyano, dialkylamino, and a solubilising group, m is 0-5 and n is 0-4, R3 is one of the following:

(i) an aryl group such as phenyl or a substituted variant thereof bearing any combination, at any one ring position, of one or more substituents such as halogen, alkyl groups containing from 1 to 10 carbon atoms, trifluoromethyl, cyano and alkoxy;

(ii) a heteroaryl group such as 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy; comprising the steps consisting of:

a) cyclisation at room temperature of a compound (IV):

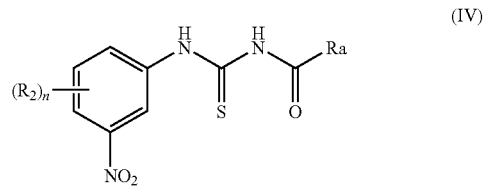

With an intermediate Int4 of formula:

Wherein Ra can be methyl, trifluoromethyl, isopropyl or a phenyl optionally substituted and R2, R3 and n are as described above, to form a compound of a (III):

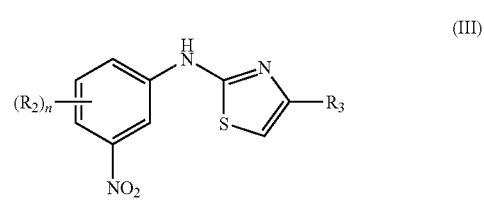

Wherein R2, R3 and n are as described above;

b) reducing the nitro group of said compound (III) to form a compound of formula II:

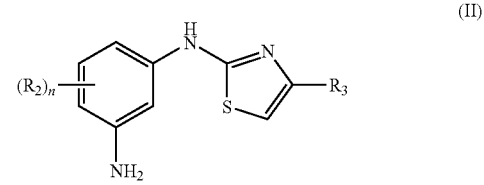

Wherein R2, R3 and n are as described above;
c) coupling in an aprotic solvent a compound of (II):
with a compound of formula Int5:

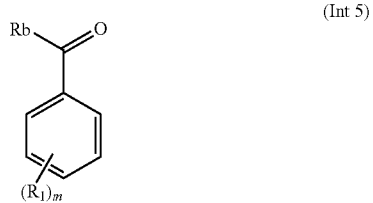
(Int 5)

Wherein Rb is a hydroxyl or alkoxy or halogen group and R1 and m are as described above, to form a compound of (I).

In one preferred embodiment, in step c) the compound (II) is treated with 3.0 equivalent of Lewis acid and is added to a solution of 1.0 equivalent of ester (Int5). Beside, the Lewis acid is trimethylaluminium.

In still another preferred embodiment, in step c) a solution of 1.0 equivalent of acid chloride (Int5) is added to a solution of 0.8 equivalent of the compound of formula II. Here, the reaction is performed in basic condition and the base can be for example triethylamine.

In still another preferred embodiments, in step c), 1.0 equivalent of the compound of formula II is coupled with 1.1 equivalent of benzoic acid (Int5). This reaction is performed using an activating agent, such as the Mukaiyama's Reagent (2-Chloro-1-methylpyridinium iodide).

In step a) the reaction mixture is diluted with water and the precipitated product is isolated by filtration.

In step b) of the method as described above, the compound of (II) obtained by reduction of the corresponding nitro compound is performed by hydrogenation. The hydrogenation can be performed with a catalyst such as Raney Nickel and the reaction is performed in a polar protic solvent such as methanol or ethanol.

In step b) the reaction mixture is diluted with water and the precipitated product is isolated by filtration.

In still another preferred embodiment, in step a), the cyclisation is performed in basic condition at a temperature between 20-30° C. The base can be potassium carbonate and the reaction is performed in a polar protic solvent such as methanol or ethanol.

The method depicted above may further comprises the step of preparing a compound of (IV), comprising the reaction of an intermediate Int1 of formula:

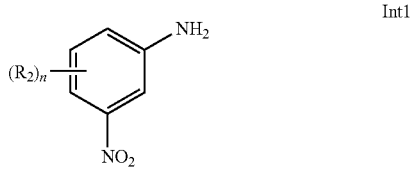
Int1

With Int2 of formula:

Int2

And Int3 of formula $NH_4SCN$,
Wherein Ra, R2 and n are as defined above.

Preferably, this reaction is performed in aprotic solvent such as acetone. Also, the reaction mixture is advantageously diluted with water and the precipitated product is isolated by filtration.

Unless otherwise specified, the below terms used herein are defined as follows:

As used herein, the term an "aryl group" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents.

In one embodiment, the aryl group is a monocyclic ring, wherein the ring comprises 6 carbon atoms, referred to herein as "(C6)aryl."

As used herein, the term "alkyl group" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents.

As used herein, the term "alkoxy" refers to an alkyl group which is attached to another moiety by an oxygen atom. Examples of alkoxy groups include methoxy, isopropoxy, ethoxy, tert-butoxy, and the like. Alkoxy groups may be optionally substituted with one or more substituents.

As used herein, the term "heteroaryl" or like terms means a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on a nitrogen may be substituted with a tert-butoxycarbonyl group. Heteroaryl groups may be optionally substituted with one or more substituents. In addition, nitrogen or sulfur heteroatom ring members may be oxidized. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings.

The term "heterocycle" as used herein, refers collectively to heterocycloalkyl groups and heteroaryl groups.

As used herein, the term "heterocycloalkyl" means a monocyclic or polycyclic group having at least one heteroatom selected from O, N or S, and which has 2-11 carbon atoms, which may be saturated or unsaturated, but is not aromatic. Examples of heterocycloalkyl groups including (but not limited to): piperidinyl, piperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyridinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein the term "substituent" or "substituted" means that a hydrogen radical on a compound or group is replaced with any desired group that is substantially stable to reaction conditions in an unprotected form or when protected using a protecting group. Examples of preferred substituents are those found in the exemplary compounds and embodiments disclosed herein, as well as halogen (chloro, iodo, bromo, or fluoro); alkyl; alkenyl; alkynyl; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); CO2CH3; CONH2; OCH2CONH2; NH2; SO2NH2; OCHF2; CF3; OCF3; and such moieties may also be optionally substituted by a fused-ring structure or bridge, for example —OCH2O—. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an aralkyl, a heteraralkyl, a haloalkyl, —C(O)NR11R12, —NR13C(O)R14, a halo, —OR13, cyano, nitro, a haloalkoxy, —C(O)R13, —NR11R12, —SR13, —C(O)OR13, —OC(O)R13, —NR13C(O)NR11R12, —OC(O)NR11R12, —NR13C(O)OR14, —S(O)rR13, —NR13S(O)rR14, —OS(O)rR14, S(O)rNR11R12, —O, —S, and —N-R13, wherein r is 1 or 2; R11 and R12, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl; or R1 and R12 taken together with the nitrogen to which they are attached is optionally substituted heterocycloalkyl or optionally substituted heteroaryl; and R13 and R14 for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted aralkyl, or an optionally substituted heteraralkyl. In certain embodiments, the term "substituent" or the adjective "substituted" refers to a solubilising group.

The term "solubilising group" means any group which can be substantially ionized and that enables the compound to be soluble in a desired solvent, such as, for example, water or water-containing solvent. Furthermore, the solubilising group can be one that increases the compound or complex's lipophilicity. Typically, the solubilising group is selected from alkyl group substituted with one or more heteroatoms such as N, O, S, each optionally substituted with alkyl group substituted independently with alkoxy, amino, alkylamino, dialkylamino, carboxyl, cyano, or substituted with cycloheteroalkyl or heteroaryl, or a phosphate, or a sulfate, or a carboxylic acid.

For example, by "solubilising group" it is referred herein to one of the following:

an alkyl, cycloalkyl, aryl, heretoaryl group comprising either at least one nitrogen or oxygen heteroatom or which group is substituted by at least one amino group or oxo group.

an amino group which may be a saturated cyclic amino group which may be substituted by a group consisting of alkyl, alkoxycarbonyl, halogen, haloalkyl, hydroxyalkyl, amino, monoalkylamino, dialkylamino, carbamoyl, monoalkylcarbamoyl and dialkylcarbamoyl.

one of the structures a) to i) shown below, wherein the wavy line and the arrow line correspond to the point of attachment to core structure of formula I.

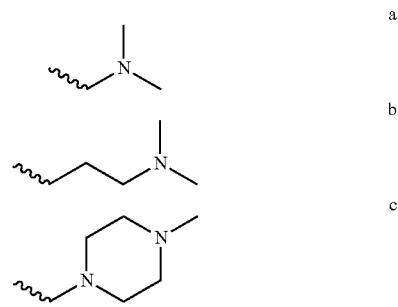

-continued

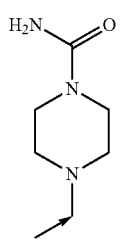

d

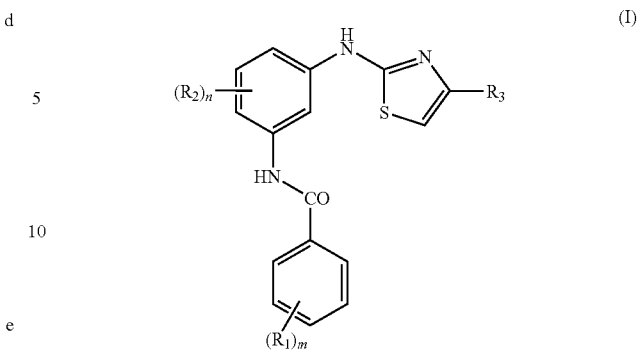

(I)

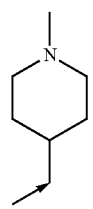

e

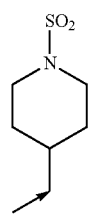

Where is:
R1 and R2 are selected independently from hydrogen, halogen, a linear or branched alkyl, cycloalkyl group containing from 1 to 10 carbon atoms, trifluoromethyl, alkoxy, amino, alkylamino, dialkylamino, solubilising group.
m is 0-5 and n is 0-4.
R3 is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, cyano and alkoxy;

f (ii) a heteroaryl group such as 2, 3, or 4-pyridyl group, which may additionally bear any combination of one or more substituents such as halogen, alkyl groups containing from 1 to 10 carbon atoms, trifluoromethyl and alkoxy;

(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

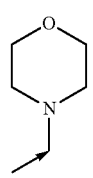

g

One aspect of the invention is method for preparing of 2-(3-aminoaryl)amino-4-aryl-thiazoles (I) or a pharmaceutical acceptable salt shown in scheme II, comprising:
a) Reacting a nitro aniline (Int1), acyl chloride (Int1) and ammonium thiocyanate (Int3) in suitable solvent to form (IV),

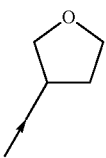

h

Wherein:
Ra can be methyl, trifluoromethyl, isopropyl or a phenyl optionally substituted.
R2 is selected independently from hydrogen, halogen, a linear or branched alkyl, cycloalkyl group containing from 1 to 10 carbon atoms, trifluoromethyl, alkoxy, amino, alkylamino, dialkylamino, solubilising group.

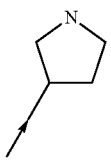

i n is 0-4.
b) Reacting a bromo ketone (Int4) with protected thiourea (IV) in suitable solvent and using suitable bases.
Substituent R3 in (Int4) and in compounds (III), (II), and (I) shown in Scheme II below is one of the following:
(i) an aryl group such as phenyl or a substituted variant thereof bearing any combination, at any one ring position, of one or more substituents such as halogen, alkyl groups containing from 1 to 10 carbon atoms, trifluoromethyl, cyano and alkoxy;
(ii) a heteroaryl group such as 2, 3, or 4-pyridyl group, which may additionally bear any combination of one or more substituents such as halogen, alkyl groups containing from 1 to 10 carbon atoms, trifluoromethyl and alkoxy;
(iii) a five-membered ring aromatic heterocyclic group such as for example 2-thienyl, 3-thienyl, 2-thiazolyl, 4-thiazolyl, 5-thiazolyl, which may additionally bear any combination of one or more substituents such as halogen, an alkyl group containing from 1 to 10 carbon atoms, trifluoromethyl, and alkoxy.

The term "cycloalkyl" means a saturated cyclic alkyl radical having from 3 to 10 carbon atoms. Representative cycloalkyls include cyclopropyl, 1-methylcyclopropyl, cyclobutyl, cyclopentyl, cyclohexyl, cycloheptyl, cyclooctyl, cyclononyl, and cyclodecyl. Cycloalkyl groups can be optionally substituted with one or more substituents.

The term "halogen" means —F, —Cl, —Br or —I.

In one particular embodiment, the invention provides a process for synthesizing an optionally substituted 2-(3-aminoaryl)amino-4-aryl-thiazoles having formula I.

Scheme II
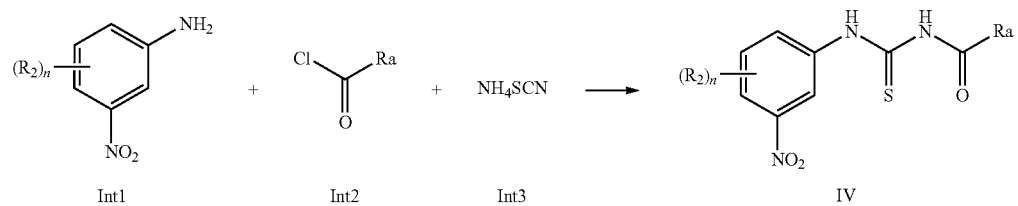
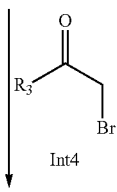
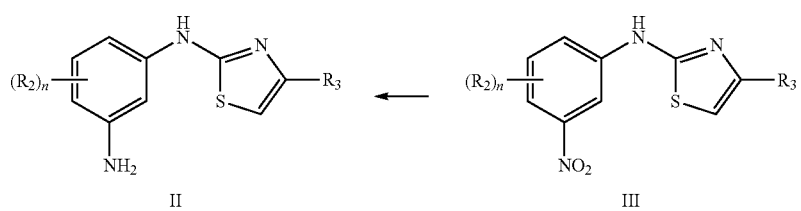
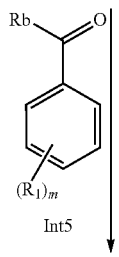
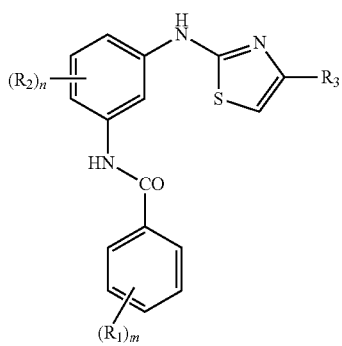

c) Reducing the nitro group of compound (III) to the corresponding amine (II) in suitable solvent.

d) Reaction aniline (II) with (Int5) using suitable coupling procedure in suitable solvent. Rb can be hydroxyl or alkoxy or halogen group.

R1 is selected independently from hydrogen, halogen, a linear or branched alkyl, cycloalkyl group containing from 1 to 10 carbon atoms, trifluoromethyl, alkoxy, amino, alkylamino, dialkylamino, solubilising group.

m is 0-5.

In still another particular embodiment, the method shown in scheme II is utilized to synthesize the compound of formula V, or a pharmaceutical acceptable salt thereof,

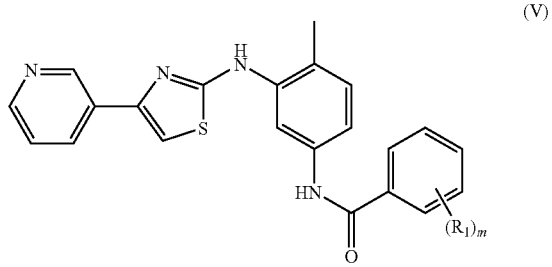
(V)

Wherein:

R1 is selected independently from hydrogen, halogen, a linear or branched alkyl, cycloalkyl group containing from 1 to 10 carbon atoms, trifluoromethyl, alkoxy, amino, alkylamino, dialkylamino, solubilising group.

m is 0-5.

Compound (VIII) can be prepared by addition of nitro aniline (int1a) to a solution of ammonium thiocyanate and acetyl chloride in aprotic solvent, preferably acetone.

Compound (VII) is obtained by cyclisation of compound (VIII) with bromoketone (Int4a) in basic condition, preferably with potassium carbonate in polar protic solvent such as methanol.

Compound (VII) is reduced to form compound (VI). Preferably, the reduction reaction is performed with a catalyst, such as a reactivated Raney Nickel. The reduction can be performed in an alcoholic or polar aprotic solvent, such as THF. According to one embodiment, the reaction is performed in the presence of hydrogen. The reaction can be also performed under phase transfer hydrogenation conditions.

Scheme III

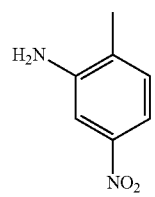
Int1a

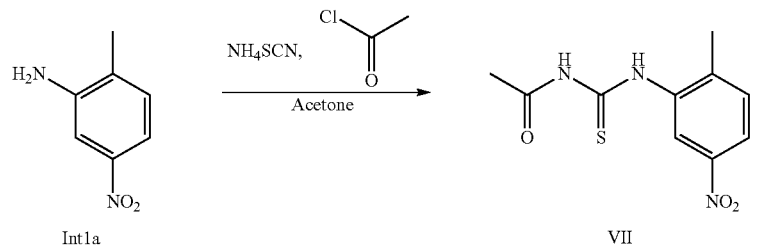
VII

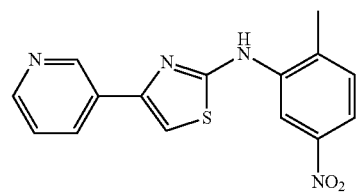
VI

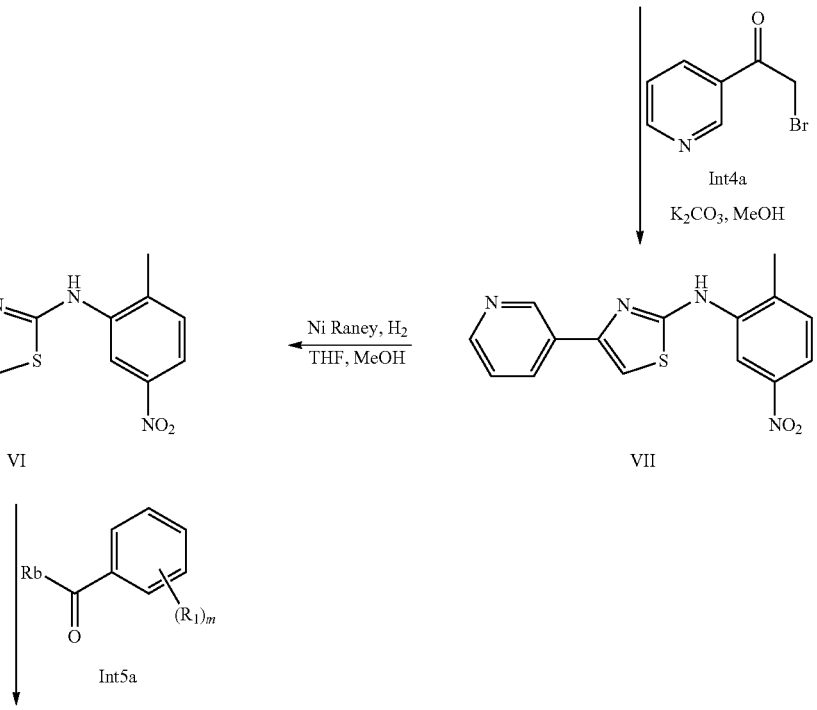

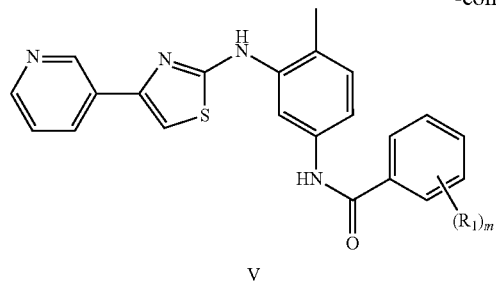

V

Compound (V) is obtained by using different conditions:
i) Wherein Rb is alkoxy group, the ester (Int5a) is coupled with (VI) using trimethylaluminium as activating agent in aprotic solvent such as dichloromethane or toluene.
ii) Wherein Rb is a halogen such as chloride, the acid chloride (Int5a) is coupled with (VI) in basic condition using preferably triethylamine in aprotic solvent such as dichloromethane.
iii) Wherein Rb is hydroxyl group, the carboxylic acid (Int5a) is coupled with (VI) using activating agents such as Mukaiyama's Reagent or HOBt/EDCI in aprotic solvent, preferably DMF.

The invention is explained in detail in the examples given below which are provided by way of illustration only and therefore should not be construed to limit the scope of the invention.

EXAMPLE 1

1-Acetyl-3-(2-methyl-5-nitro-phenyl)-thiourea

In a reactor, introduce ammonium thiocyanate (25 kg, 328.43 mol), acetyle chloride (24 kg, 337.53 mol), acetone (225 L) and 2-methyl-5-nitroaniline (Int1) (42 kg, 276.04 mol). Temperature was maintained at 25±10° C. for approximately 4 hours. Water (413 L) was added and reaction mixture was stirred for approximately 1 hour. The precipitate filtered, washed with water and diisopropylether. The product was then dried in a tray drier at 45-50° C.

Yield=84%.

$^1$H NMR (DMSO-$d_6$): δ=12.37 (1H, s); 11.68 (1H, s); 8.68 (1H, d, J=2.5 Hz); 8.06 (1H, dd, J=8.4, 2.5 Hz); 7.58 (1H, d, J=8.4 Hz); 2.33 (3H, s); 2.18 (3H, s).

MS (ES$^+$) m/z=254.1 (M+H)$^+$; (ES$^-$) m/z=252.3 (M−H)$^-$.
Mp=205° C.

EXAMPLE 2

(2-Methyl-5-nitro-phenyl)-(4-pyridin-3-yl-thiazol-2-yl)-amine

In a reactor, introduce methanol (1120 L), potassium carbonate (287 kg, 2076.70 mol) and 1-acetyl-3-(2-methyl-5-nitro-phenyl)-thiourea (67 kg, 264.53 mol). 2-bromo-1-pyridin-3-yl-ethanone (Int4) (52 kg, 259.96 mol) was then added and temperature maintained at 25-30° C. for 4 hours. Water (692 L) was added to the reaction mixture and precipitate filtered, washed with water and diisopropylether. The product was then dried in a tray drier at 45-50° C.

Yield=95%.

$^1$H NMR (DMSO-$d_6$): δ=9.83 (1H, s); 9.60 (1H, d, J=2.5 Hz); 9.18 (1H, d, J=1.9 Hz); 8.53 (1H, dd, J=4.6, 1.5 Hz); 8.27 (1H, dt, J=8.0, 1.9 Hz); 7.80 (1H, dd, J=8.2, 2.5 Hz); 7.66 (1H, s); 7.48 (2H, m); 2.44 (3H, s).

MS (ES$^+$) m/z=313.1 (M+H)$^+$; (ES$^-$) m/z=311.3 (M−H)$^-$.
Mp=225° C.

EXAMPLE 3

4-Methyl-N3-(4-pyridin-3-yl-thiazol-2-yl)-benzene-1,3-diamine

In a reactor, a mixture of (2-methyl-5-nitro-phenyl)-(4-pyridin-3-yl-thiazol-2-yl)-amine (40 kg, 128.06 mol), Raney Nickel (2.7 kg, 46.00 mol) and methanol (600 L), was warmed to 40-45° C. and hydrogenated under hydrogen pressure (5 kg/cm$^2$) for 2 hours. The reaction mixture was filtered and concentrated. Water was added to the residue under stirring. The product was then filtered and dried in a tray drier at 45-50° C.

Yield=85%.

$^1$H NMR (DMSO-$d_6$): δ=9.20 (1H, s); 9.09 (1H, dd, J=2.3, 0.76 Hz); 9.48 (1H, dd, J=4.8, 1.7 Hz); 8.20 (1H, dt, J=8.0, 2.1 Hz); 7.42 (1H, ddd, J=7.8, 4.8, 0.8 Hz); 7.38 (1H, s); 7.09 (1H, d, J=2.3 Hz); 6.85 (1H, d, J=8.0 Hz); 6.29 (1H, dd, J=8.0, 2.3 Hz); 4.95 (1H, s); 2.10 (3H, s).

MS (ES$^+$) m/z=283.1 (M+H)$^+$; (ES) m/z=281.4.
Mp=136° C.

EXAMPLE 4

N-[4-Methyl-3-(4-pyridin-3-yl-thiazol-2-ylamino)-phenyl]-benzamide derivatives

Method A

In a reactor and under low nitrogen pressure, add 4-Methyl-N3-(4-pyridin-3-yl-thiazol-2-yl)-benzene-1,3-diamine (95 g, 336.45 mmol), dichloromethane (2 L). To this suspension cooled to temperature of 5° C. was added dropwise 2M/n-hexane solution of trimethylaluminium (588 mL). The reaction mixture was brought progressively to 15° C., and maintained for 2 h under stirring. 4-(4-Methyl-piperazin-1-ylmethyl)-benzoic acid methyl ester (100 g, 402.71 mmol) in dichloromethane (200 mL) was added for 10 minutes. After 1 h stirring at room temperature, the reaction mixture was heated to reflux for 20 h and cooled to room temperature. This solution was transferred dropwise via a cannula to a reactor containing 2N NaOH (2.1 L) cooled to 5° C. After stirring for 3 h at room temperature, the precipitate was filtered through Celite. The solution was extracted with dichloromethane and the organic layer was washed with water and saturated sodium chloride solution, dried over $MgSO_4$ and concentrated under vacuum. The brown solid obtained was recrystallized from i-$Pr_2O$ to give 130.7 g (78%) of a beige powder.
Method B
Preparation of the Acid Chloride To a mixture of 4-(4-Methyl-piperazin-1-ylmethyl)-benzoic acid dihydrochloride (1.0 eq), dichloromethane (7 vol) and triethylamine (2.15 eq), thionyl chloride (1.2 eq) was added at 18-28° C. The reaction mixture was stirred at 28-32° C. for 1 hour.
Coupling of Acid Chloride with Amino Thiazole To a chilled (0-5° C.) suspension of 4-Methyl-N3-(4-pyridin-3-yl-thiazol-2-yl)-benzene-1,3-diamine (0.8 eq) and thiethylamine (2.2 eq) in dichloromethane (3 vol), the acid chloride solution (prepared above) was maintaining the temperature below 5° C. The reaction mixture was warmed to 25-30° C. and stirred at the same temperature for 10 h. Methanol (2 vol) and water (5 vol) were added to the reaction mixture and stirred. After separating the layers, methanol (2 vol), dihloromethane (5 vol) and sodium hydroxide solution (aqueous, 10%, till pH was 9.5-10.0) were added to the aqueous layer and stirred for 10 minutes. The layers were separated. The organic layer was a washed with water and saturated sodium chloride solution. The organic layer was concentrated and ethanol (2 vol) was added and stirred. The mixture was concentrated. Ethanol was added to the residue and stirred. The product was filtered and dried at 50-55° C. in a vaccum tray drier.

Yield=65-75%.
Method C

To a solution of 4-methyl-N3-(4-pyridin-3-yl-thiazol-2-yl)-benzene-1,3-diamine (1.0 eq) in DMF (20 vol) were added successively triethylamine (5 eq), 2-chloro-1-methylpyridinium iodide (2 eq) and 4-(4-methyl-piperazin-1-ylmethyl)-benzoic acid (2 eq). The reaction mixture was stirred for 7 h at room temperature. Then, the mixture was diluted in diethyl ether and washed with water and saturated aqueous $NaHCO_3$, dried over $Na_2SO_4$ and concentrated. The crude product was purified by column chromatography using an elution of 100% EtOAc to give a yellow solid.

Yield=51%.

$^1H$ NMR ($CDCl_3$): δ=9.09 (1H, s, NH); 8.52 (1H, br s); 8.27 (1H, s); 8.13 (1H, s); 8.03 (1H, s); 7.85 (2H, d, J=8.3 Hz); 7.45 (2H, m); 7.21-7.38 (4H, m); 6.89 (1H, s); 3.56 (2H, s); 2.50 (8H, br s); 2.31 (6H, br s).

MS (CI) m/z=499 (M+H)$^1$.

An additional aspect of the present invention relates to a particular polymorph of the methanesulfonic acid salt of N-[4-Methyl-3-(4-pyridin-3-yl-thiazol-2-ylamino)-phenyl]-benzamide of formula (IX).

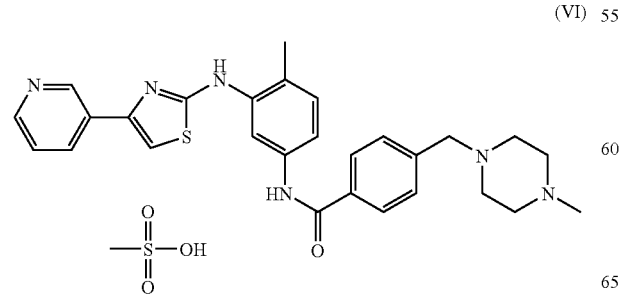

(VI)

Hereinafter is described the polymorph form of (IX) which has the most advantageous properties concerning processability, storage and formulation. For example, this form remains, dry at 80% relative humidity and thermodynamically stable at temperatures below 200° C.

Figure 2:
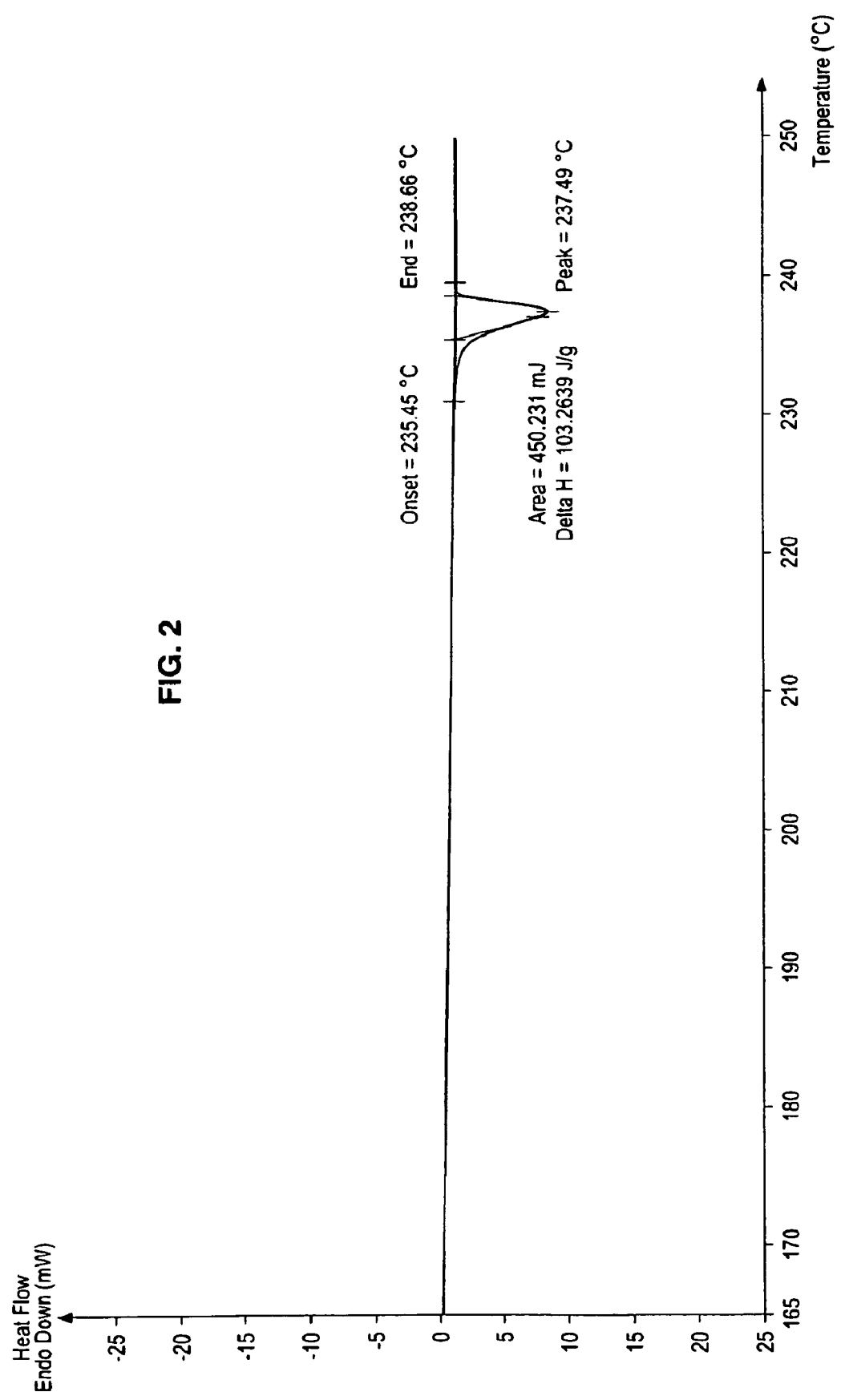
FIG. 2 shows a differential scanning calorimetry (DSC) of a polymorph of the methanesulfonic acid salt of N-[4-Methyl-3-(4-pyridin-3-yl-thiazol-2-ylamino)-phenyl]-benzamide of formula (IX).

The polymorph of this form is characterized by an X-ray diffraction pattern illustrated in FIG. 1, comprising characteristic peaks approximately 7.269, 9.120, 11.038, 13.704, 14.481, 15.483, 15.870, 16.718, 17.087, 17.473, 18.224, 19.248, 19.441, 19.940, 20.441, 21.469, 21.750, 22.111, 23.319, 23.763, 24.120, 24.681, 25.754, 26.777, 28.975, 29.609, 30.073 degrees θ, and is also characterized by differential scanning calorimetry (DSC) illustrated in FIG. 2, which exhibit a single maximum value at approximately 237.49±0.3° C.

X-ray diffraction pattern is measured using a Bruker AXS (D8 advance). Differential scanning calorimetry (DSC) is measured using a Perking Elmer Precisely (Diamond DSC).

This polymorph form can be obtained by treatment of 4-(4-Methyl-piperazin-1-ylmethyl)-N-[4-methyl-3-(4-pyridin-3-yl-thiazol-2-ylamino)-phenyl]-benzamide with 1.0 to 1.2 equivalent of methanesulfonic acid, at a suitable temperature, preferably between 20-80° C.

The reaction is performed in a suitable solvent especially polar solvent such as methanol or ethanol, or ketone such as acetone, or ether such as diethylether or dioxane, or a mixture thereof.

This invention is explained in example given below which is provided by way of illustration only and therefore should not be construed to limit the scope of the invention.

Preparation of the above-mentioned polymorph form of 4-(4-Methyl-piperazin-1-ylmethyl)-N-[4-methyl-3-(4-pyridin-3-yl-thiazol-2-ylamino)-phenyl]-benzamide methanesulfonate.

4-(4-Methyl-piperazin-1-ylmethyl)-N-[4-methyl-3-(4-pyridin-3-yl-thiazol-2-ylamino)-phenyl]-benzamide (1.0 eq) was dissolved in ethanol (4.5 vol) at 65-70° C. Methanesulfonic acid (1.0 eq) was added slowly at the same temperature. The mixture was cooled to 25-30° C. and maintained for 6 h. The product was filtered and dried in a vacuum tray drier at 55-60° C. Yield=85-90%. Starting melting point Smp=236° C.

The invention claimed is:
1. A process for manufacturing a compound of formula (I):

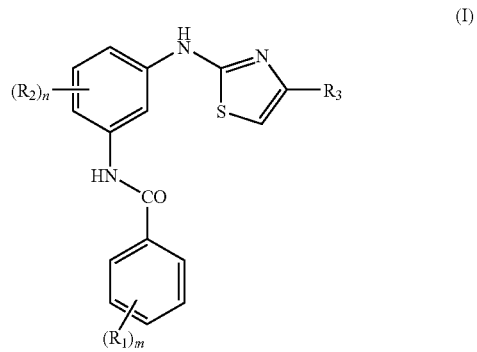

(I)

or a salt thereof, wherein each of $R_1$ and $R_2$ is one substituent selected from the group consisting of hydrogen, halogen, a linear or branched alkyl, cycloalkyl group containing from 1 to 10 carbon atoms, trifluoromethyl, alkoxy, cyano, dialkylamino, and a solubilising group, the substituents for $R_1$ and $R_2$ being selected independently from one another, m is 0-5 and n is 0-4, $R_3$ is one of the following (i)-(iii):

(i) an aryl group optionally substituted with at least one substituent selected from the group consisting of a halogen, an alkyl group containing from 1 to 10 carbon atoms, trifluoromethyl, cyano and alkoxy;

(ii) a heteroaryl group optionally substituted with at least one substituent selected from the group consisting of a halogen, an alkyl group containing from 1 to 10 carbon atoms, trifluoromethyl and alkoxy;

(iii) a five-membered ring aromatic heterocyclic group optionally substituted with at least one substituent selected from the group consisting of a halogen, an alkyl group containing from 1 to 10 carbon atoms, trifluoromethyl, and alkoxy;

the process comprising:

a) cyclizing, at room temperature, a compound of formula (IV):

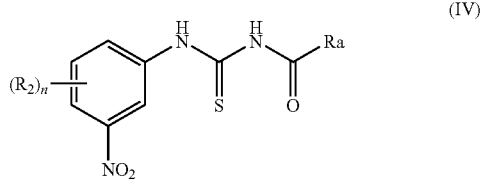

with an intermediate of formula (Int4):

wherein Ra can be methyl, trifluoromethyl, isopropyl or a phenyl optionally substituted and $R_2$, $R_3$ and n are as described above, to form a compound of formula (III):

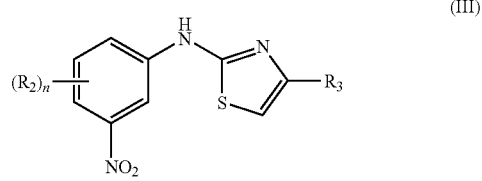

wherein $R_2$, $R_3$ and n are as described above;

b) reducing the nitro group of said compound of formula (III) to form a compound of formula (II):

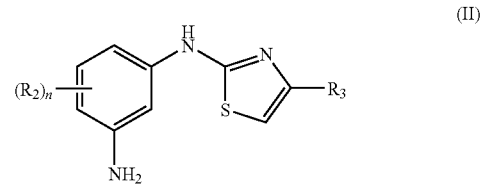

wherein $R_2$, $R_3$ and n are as described above; and c) coupling, in an aprotic solvent, the compound of formula (II) with a compound of formula (Int5)

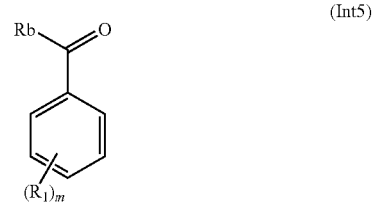

wherein Rb is a hydroxyl, an alkoxy or a halogen group and $R_1$ and m are as described above, to form the compound of formula (I).

2. The process of claim 1, wherein in step c), the compound of formula (II) is treated with 3.0 equivalent of Lewis acid and is added to a solution of 1.0 equivalent of the compound of formula (Int5), where Rb is an alkoxy group.

3. The process of claim 2, wherein the Lewis acid is trimethylaluminium.

4. The process of claim 1, wherein in step c), a solution of 1.0 equivalent of the compound of formula (Int5) is added to a solution of 0.8 equivalent of the compound of formula (II), where Rb is chloride.

5. The process of claim 4, wherein the reaction in step c) is performed in a basic condition.

6. The process of claim 5, wherein the reaction in step c) is performed in the presence of triethylamine.

7. The process of claim 1, wherein in step c), 1.0 equivalent of the compound of formula (II) is coupled with 1.1 equivalent of the compound of formula (Int5), where Rb is a hydroxyl group.

8. The process of claim 7, wherein the reaction in step is performed using an activating agent.

9. The process of claim 8, wherein the activating agent is Mukaiyama's Reagent (2-chloro-1-methylpyridinium iodide).

10. The process according to claim 1, wherein in step a), the reaction mixture is diluted with water and a precipitated product is isolated by filtration.

11. The process according to claim 1, wherein in step b), the the nitro group of the compound of formula (III) is reduced by a hydrogenation reaction.

12. The process of claim 11, wherein the hydrogenation reaction is performed with a catalyst.

13. The process of claim 12, wherein the catalyst is Raney Nickel.

14. The process of claim 11, wherein the hydrogenation reaction in step b) is performed in a polar protic solvent.

15. The process according to claim 11, wherein in step b), the reaction mixture is diluted with water and a precipitated product is isolated by filtration.

16. The process according to claim 1, wherein in step a), the cyclisation is performed in a basic condition at a temperature between 20-30° C.

17. The process of claim 16, wherein the cyclisation in step a) is performed in the presence of potassium carbonate.

18. The process of claim 16, wherein the reaction in step a) is performed in a polar protic solvent.

19. The process according to claim 1, further comprising d) preparing a compound of formula (IV) by reacting an intermediate of formula (Int1):

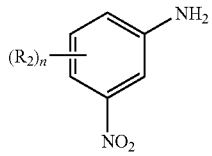

with a compound of formula (Int2):

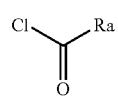

and NH$_4$SCN,
wherein Ra, R$_2$ and n are as defined in claim 1.

20. The process of claim 19, wherein in step d), the reaction is performed in an aprotic solvent.

21. The process according to claim 19, wherein in step d), the reaction mixture is diluted with water and a precipitated product is isolated by filtration.

22. The process of claim 1, wherein the compound of formula (I) is 4-(4-methyl-piperazin-1-ylmethyl)-N-[4-methyl-3-(4-pyridin-3-yl-thiazol-2-ylamino)-phenyl]-benzamide.

* * * * *